United States Patent
Tseng et al.

(10) Patent No.: US 11,266,385 B1
(45) Date of Patent: Mar. 8, 2022

(54) CONTROL OF MULTIPLE GENERATORS FOR SURGICAL DEVICES

(71) Applicant: Verily Life Sciences LLC, South San Francisco, CA (US)

(72) Inventors: Jonathan Tseng, Mountain View, CA (US); James Shuma, San Jose, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 7 days.

(21) Appl. No.: 16/430,838

(22) Filed: Jun. 4, 2019

(51) Int. Cl.
*A61B 17/00* (2006.01)
*A61B 34/00* (2016.01)
*A61B 18/12* (2006.01)

(52) U.S. Cl.
CPC .............. *A61B 17/00* (2013.01); *A61B 34/76* (2016.02); *A61B 18/1206* (2013.01); *A61B 2017/00119* (2013.01); *A61B 2017/00371* (2013.01); *A61B 2017/00973* (2013.01); *A61B 2560/0276* (2013.01); *A61B 2562/0257* (2013.01)

(58) Field of Classification Search
CPC ........... A61B 2017/00973; A61B 2017/00225; A61B 18/1206; A61B 2017/00199; A61B 2017/00212; A61B 2562/0257; A61B 34/25
See application file for complete search history.

(56) References Cited

U.S. PATENT DOCUMENTS

| 8,120,301 | B2 | 2/2012 | Goldberg et al. |
| 2012/0078139 | A1 | 3/2012 | Aldridge et al. |
| 2018/0280099 | A1* | 10/2018 | Cone et al. ............ A61B 34/74 |
| 2019/0142530 | A1* | 5/2019 | Thompson et al. ... A61B 34/25 |

* cited by examiner

*Primary Examiner* — Carl H Layno
*Assistant Examiner* — Aya Ziad Bakkar
(74) *Attorney, Agent, or Firm* — Kilpatrick Townsend & Stockton LLP

(57) ABSTRACT

A method for controlling a plurality of surgical devices includes: receiving a foot pedal signal indicating a foot pedal activation of a first foot pedal of a plurality of foot pedals; generating a control signal based on the foot pedal signal, wherein: if the foot pedal signal indicates that only the first foot pedal is pressed, then generating the control signal to cause a generator to activate a first surgical device associated with the first foot pedal; if the foot pedal signal indicates that the first foot pedal remains pressed and a second foot pedal is newly pressed, then generating the control signal to cause the generator to: maintain activation of the first surgical device associated with the first foot pedal; and not activate a second surgical device associated with the second foot pedal; and outputting the control signal to the generator.

42 Claims, 5 Drawing Sheets

CONTROL OF MULTIPLE GENERATORS FOR SURGICAL DEVICES

FIELD

The present disclosure relates generally to the control of multiple separate generators. More specifically, but not by way of limitation, this disclosure relates to devices and methods for controlling multiple separate generators that are used to activate multiple surgical devices connected to a single surgical platform.

BACKGROUND

Generators are used during surgery to provide energy to surgical devices. In some instances, a surgery may require multiple generators to power multiple surgical devices, e.g., a generator for delivering core energy to surgical devices and a generator for delivering advanced energy to surgical devices. Typically, the multiple generators are external, separate, third-party generators that are not equipped to communicate with one another. Using multiple generators to power multiple surgical devices raises safety considerations and technical challenges in preventing the multiple generators from activating multiple surgical devices simultaneously.

SUMMARY

Various examples are described for devices and methods for controlling multiple separate generators that are used to activate multiple surgical devices connected to a single surgical platform. One example method includes receiving a foot pedal signal indicating a foot pedal activation of a first foot pedal of a plurality of foot pedals; generating a control signal based on the foot pedal signal, wherein: if the foot pedal signal indicates that only the first foot pedal is pressed, then generating the control signal to cause a generator to activate a first surgical device associated with the first foot pedal; if the foot pedal signal indicates that the first foot pedal remains pressed and a second foot pedal is newly pressed, then generating the control signal to cause the generator to: maintain activation of the first surgical device associated with the first foot pedal; and not activate a second surgical device associated with the second foot pedal; and if the foot pedal signal indicates that the first foot pedal is released while the second foot pedal remains pressed, then generating the control signal to cause the generator to: deactivate the first surgical device associated with the first foot pedal, and not activate the second surgical device associated with the second foot pedal; and outputting the control signal to the generator.

One example system includes a plurality of foot pedals; at least one generator; and at least one processor communicatively coupled to the plurality of foot pedals and the at least one generator, the at least one processor configured to: receive a foot pedal signal indicating a foot pedal activation of a first foot pedal of the plurality of foot pedals; generate a control signal based on the foot pedal signal, wherein: if the foot pedal signal indicates that only the first foot pedal is pressed, then generating the control signal to cause the at least one generator to activate a first surgical device associated with the first foot pedal; if the foot pedal signal indicates that the first foot pedal remains pressed and a second foot pedal is newly pressed, then generating the control signal to cause the at least one generator to: maintain activation of the first surgical device associated with the first foot pedal; and not activate a second surgical device associated with the second foot pedal; and if the foot pedal signal indicates that the first foot pedal is released while the second foot pedal remains pressed, then generating the control signal to cause the at least one generator to: deactivate the first surgical device associated with the first foot pedal; and not activate the second surgical device associated with the second foot pedal; and outputting the control signal to the at least one generator.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
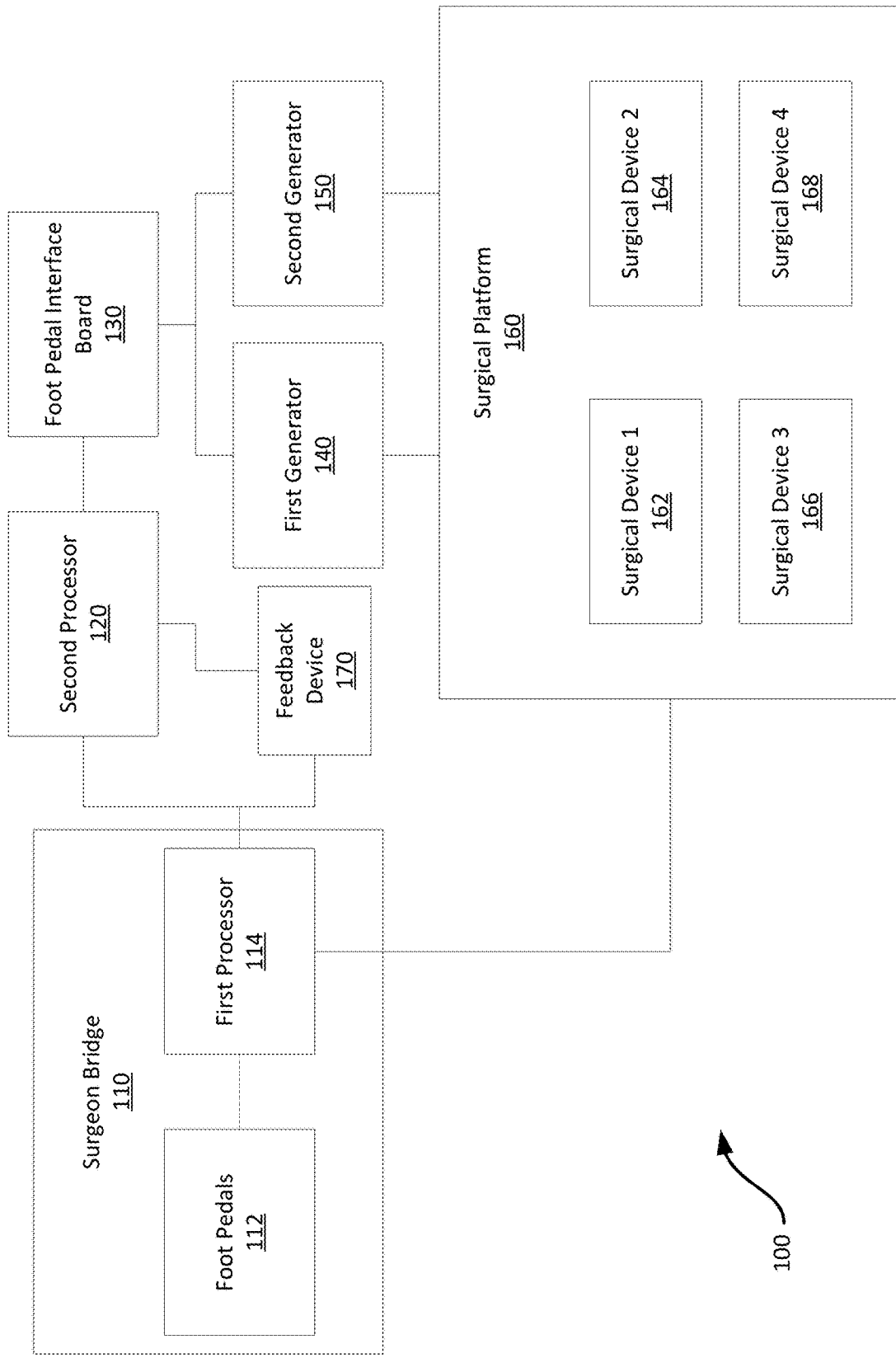
FIG. 1 shows an example system for controlling multiple separate generators that are used to activate multiple surgical devices connected to a single surgical platform according to this disclosure.

Examples are described herein in the context of devices and methods for controlling multiple separate generators that are used to activate multiple surgical devices connected to a single surgical platform. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

To provide consistent and predictable surgical practices, it may be desirable to control multiple separate generators that are used to activate multiple surgical devices connected to a single surgical platform. Examples according to this disclosure can provide for the control of multiple separate generators that are used to activate multiple surgical devices connected to a single surgical platform.

In an illustrative example, a surgical system includes a surgeon console that the surgeon interacts with during a surgery. The surgeon console includes at least two foot pedals that a surgeon can press to activate different energy tools as needed during a surgery. The pedals provide signals to a processor that then determines which energy tool to activate or deactivate.

One of the problems surgeons encounter using foot pedals is that the surgeon may inadvertently press two (or more) pedals at the same time. In general, only one energy tool should be used at a time. Thus, activating a second energy tool may be unexpected by the surgeon, especially if the pedal press was inadvertent, and may injure the patient. Thus, the system includes software to properly manage foot pedal presses to ensure that only one energy tool is active at a time, even if multiple foot pedals are pressed.

For example, if the foot pedal signal indicates that only a single foot pedal is pressed, the software will generate a control signal to activate the surgical device corresponding to the pressed foot pedal. But if the foot pedal signal indicates that a first foot pedal is pressed and remains pressed while a second foot pedal is newly pressed, then the software will generate a control signal that causes the one generator to remain active but does not activate the surgical device that is associated with the second foot pedal. Further, to ensure smooth and intentional transitions between energy tools, the software will not allow transition to a different energy pedal unless certain conditions are met. In this case, if the foot pedal signal indicates that the first foot pedal is released while the second foot pedal remains pressed, then the software will generate a control signal to deactivate the surgical device associated with the first foot pedal and to not activate the surgical device that is associated with the second foot pedal. In other words, if the surgeon wants to switch energy tools, she must deactivate one tool before attempting to activate a different tool.

One advantage of using this software to control the activation of the surgical devices via the generators is that it ensures that at most only one surgical device will be activated. In addition, this software also allows for a consistent approach to handling multiple foot pedal presses even when multiple separate, external generators not capable of communicating between each other are used. Additionally, the software meets clinical requirements for how to handle multiple foot pedal presses (e.g. if a first pedal is pressed and a second pedal is pressed, the generator maintains the activation of the surgical device corresponding to the first pedal until the first pedal is released after which no surgical device is activated).

This illustrative example is given to introduce the reader to the general subject matter discussed herein and the disclosure is not limited to this example. The following sections describe various additional non-limiting examples and examples of systems and methods for controlling multiple separate generators that are used to activate multiple surgical devices connected to a single surgical platform.

Referring now to FIG. 1, FIG. 1 shows an example system 100 for controlling multiple separate generators that are used to activate multiple surgical devices connected to a single surgical platform. The system 100 includes a surgeon console 110, which includes multiple foot pedals 112 and a first processor 114, a second processor 120, a foot pedal interface board 130, a first generator 140, a second generator 150, a surgical platform 160, which includes a first surgical device 162, a second surgical device 164, a third surgical device 166, and a fourth surgical device 168, and a feedback device 170.

Figure 2:
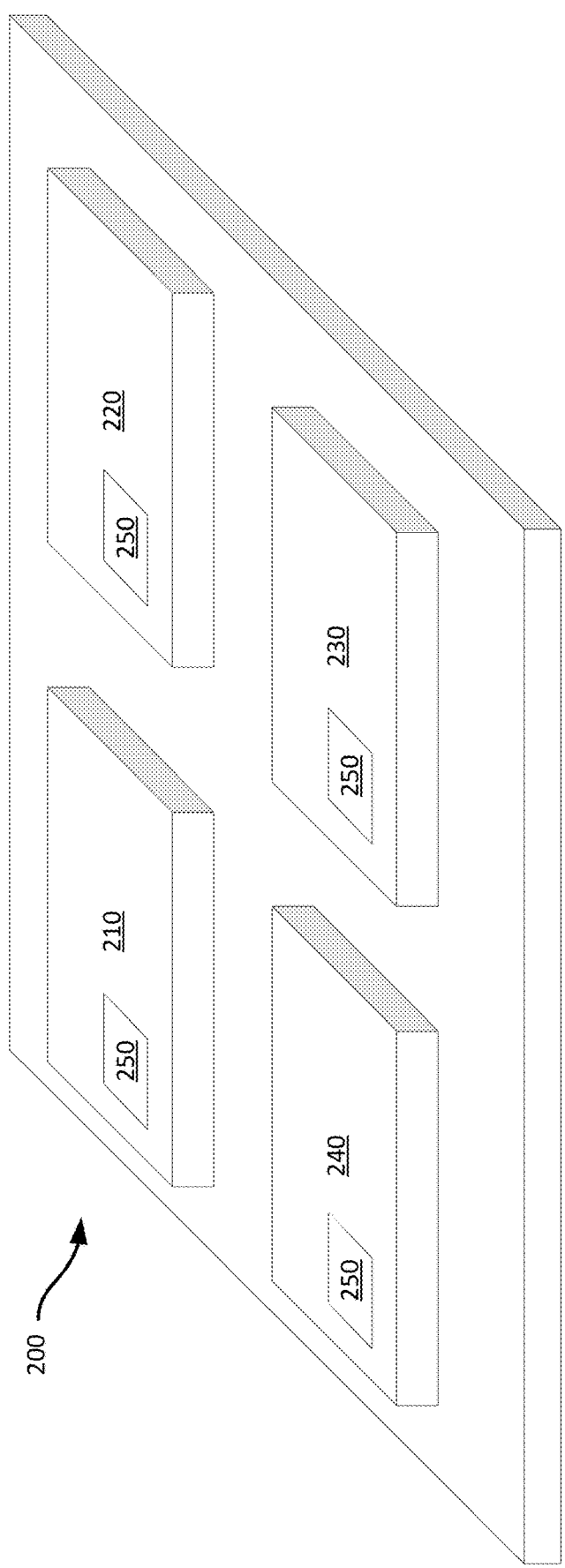
FIG. 2 shows an example foot pedal device used for controlling multiple separate generators that are used to activate multiple surgical devices connected to a single surgical platform according to this disclosure.

In some examples, the surgeon console 110 is where a surgeon may sit to control the activation of the surgical devices of the surgical platform 160 using the foot pedals 112. An example of a foot pedal device is shown in FIG. 2. The example foot pedal device 200 includes four separate foot pedals, first foot pedal 210, second foot pedal 220, third foot pedal 230, and fourth foot pedal 240. The foot pedals 210-240 are arranged in a two-by-two pattern on the foot pedal device 200. However, the foot pedals 210-240 may be arranged in any suitable pattern and may be organized in any suitable order, e.g., the first foot pedal 210 may be in the lower left hand corner of the foot pedal device 200, the second foot pedal 220 may be in the upper left hand corner of the foot pedal device 200, the third foot pedal 230 may be in the upper right hand corner of the foot pedal device 200, and the fourth foot pedal 240 may be in the lower right hand corner of the foot pedal device 200. Additionally, the foot pedal device 200 may include any suitable number of foot pedals, such as one foot pedal, two foot pedals, three foot pedals, etc.

The foot pedals 210-240 each include a proximity sensor 250. In some examples the proximity sensor 250 may be an optical sensor. The proximity sensor 250 may detect whether an object, such as a user's foot, is located near the foot pedal 210-240, e.g., a surgeon's foot is hovering over the pedal. The proximity sensor 250 transmits sensor signals to either the first processor 114 or the second processor 120 to indicate whether the proximity sensor 250 detects the presence of an object near or proximate to one of the foot pedals 210-240. In some examples, the proximity sensor 250 may not be included on each of the foot pedals 210-240 found on the foot pedal device 200. In other examples, the foot pedal device 200 may not include any proximity sensors 250 on the foot pedals 210-240.

In some examples, the proximity sensors 250 may provide the sensor signals to indicates that an object, e.g., the surgeon's foot, is near the pedal or the sensor signals may be used in conjunction with a foot pedal signal generated by the foot pedals 210-240, or in some examples by the foot pedal device 200, to detect a possible error condition relating to the pressing of one or more foot pedals 210-240. For example, if the foot pedal signal indicates a pedal press, but the sensor signal indicates that no object is in the proximity of the pressed pedal, an error may be detected and communicated to the surgeon or other staff in an operating room.

Referring again to FIG. 1, the foot pedals 112 may be the foot pedals 210-240 of the foot pedal device 200 discussed in relation to FIG. 2. In some examples, the foot pedals 112 may include multiple foot pedal devices 200, each having one or more foot pedals 210-240 as described above.

The foot pedals 112 or the foot pedal device 200 may be communicatively coupled to the first processor 114 using any suitable wired or wireless connection, such as a USB cable, Ethernet, IEEE 1394, IEEE 802.11, Bluetooth, radio interfaces for accessing cellular telephone networks (e.g., transceiver/antenna for accessing a CDMA, GSM, UMTS, or other mobile communications network(s)), etc. For example, the foot pedals 112 may be communicatively coupled to the first processor 114 using a USB cable. Thus, when one or more foot pedals are pressed by a surgeon, the foot pedal device 200 transmits one or more foot pedal signals to the first processor 114 via the USB connection to indicate that the one or more foot pedals are pressed. These foot pedal signals may be used to determine which surgical device 162-168 should be activated or deactivated.

The first processor 114 is communicatively coupled to the second processor 120, again using any suitable wired or wireless connection as described above. For example, the first processor 114 may be communicatively coupled to the second processor 120 via a local area network. As described earlier in reference to FIG. 2, the first processor 114 or the second processor 120 may also receive sensor signals from the proximity sensor 250. The processor 114 or 120 may then generate an error feedback signal based in part on the sensor signal and the foot pedal signal when the signals indicate that the foot pedal is pressed while the presence of an object is not detected in the proximity of the pressed foot pedal. The error feedback signal may then be output to the feedback device 170. The feedback device 170 may be configured to output any suitable form of feedback, including audio feedback, visual feedback, tactile feedback, etc. Additionally, while the feedback device 170 is shown as a separate device in FIG. 1, the feedback device 170 may be incorporated into any of the devices included in the system 100, such as the surgeon console 110, the foot pedals 112, the foot pedal interface board 130, the first generator 140, the second generator 150, the surgical platform 160, the first surgical device 162, the second surgical device 164, the third surgical device 166, the fourth surgical device 168, etc.

In some examples, the first processor 114 and the second processor 120 are separate from one another, as is shown in FIG. 1. The separate first processor 114 and second processor 120 may be integrated into two separate computing devices 500, where the computing device 500 is discussed in more detail below in reference to FIG. 5, or the first processor 114 and the second processor 120 may be integrated into a single computing device 500. Additionally, any suitable number of separate processors may be added and incorporated into the system 100, e.g., a third processor, a fourth processor, a fifth processor, etc. While FIG. 1 shows the first processor 114 and the second processor 120, it is also understood that only a single processor may be used in the system 100 to control multiple separate generators that are used to activate multiple surgical devices connected to a single surgical platform.

In some examples, the first processor 114 may also be communicatively coupled to the surgical platform 160. The surgical platform 160 includes a plurality of surgical devices, e.g., a first surgical device 162, a second surgical device 164, a third surgical device 166, and a fourth surgical device 168. In some examples, each surgical device 162-168 may be mechanically coupled to a robotic arm that can control the movement and positioning of the surgical devices 162-168. While FIG. 1 shows four surgical devices as part of the surgical platform 160, any suitable number of surgical devices may be included on the surgical platform 160, e.g., fewer than four pedals, or examples that may include a fifth surgical device, a sixth surgical device, a seventh surgical device, etc. Typically, the number of surgical devices included on the surgical platform 160 corresponds to the number of foot pedals 112 in the system 100; however, in some systems, the number of surgical devices included on the surgical platform 160 may differ from the number of foot pedals 112.

The first processor 114 may receive at least one surgical device signal from the surgical platform 160. The surgical device signal may indicate which surgical device is associated with which foot pedal 112. The surgical device signal may also indicate that the surgical devices 162-168 are correctly connected to the surgical platform 160 and are functioning properly.

In some examples, the second processor 120 determines and generates a control signal based on the foot pedal signal. The control signal may be determined and generated using software implemented by the second processor 120. For example, the state machine shown in FIG. 3, and discussed in further detail below, may be implemented by the second processor 120 to determine and generate the control signal.

The second processor 120 is communicatively coupled to a foot pedal interface board 130, and the foot pedal interface board 130 is communicatively coupled to a first generator 140 and a second generator 150. While only two generators 140, 150 are shown in FIG. 1, any suitable number of generators may be used to power the surgical devices 162-168 of the surgical platform 160, e.g., a third generator, a fourth generator, a fifth generator, etc. The foot pedal interface board 130 receives the control signal from the second processor 120 and transmits the control signal to one or more of the first generator 140 or the second generator 150 based on the control signal. The first generator 140 and the second generator 150 may then output a suitable energy type, e.g., monopolar core energy, bipolar core energy, or advanced energy, to a single or multiple surgical device(s) 162-168 to either activate or de-activate the surgical devices 162-168 so that only a single surgical device is activated at one time.

Figure 3:
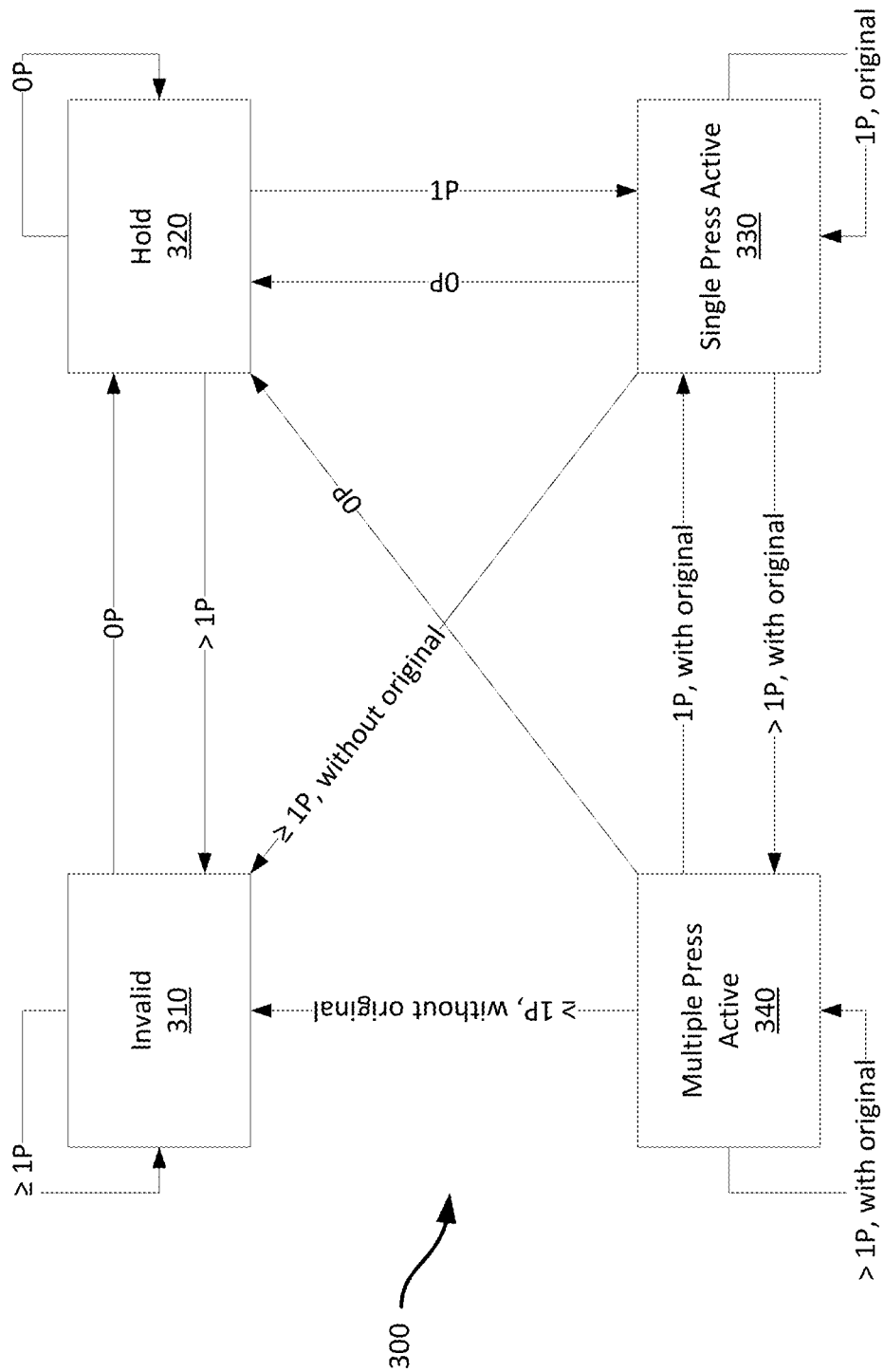
FIG. 3 shows an example state machine implemented in a processor for controlling multiple separate generators that are used to activate multiple surgical devices connected to a single surgical platform according to this disclosure.

Referring now to FIG. 3, FIG. 3 shows an example state machine 300 for controlling multiple separate generators that are used to activate multiple surgical devices connected to a single surgical platform. As discussed above in relation to FIG. 1, the state machine 300 may be implemented in a processor, such as second processor 120, so that the state machine 300 functions as part of the system 100. The state machine 300 in this example has four different states: an invalid state 310, a hold state 320, a single press active state 330, and a multiple press active state 340. However, the state machine 300 may have any suitable number of states, e.g., one, two, three, five, six, etc. The state machine 300 transitions from a first state to a second state based on the foot pedal signal received by the second processor 120 and generates a control signal to transmit to the foot pedal interface board 130 based on the transition between the states.

In some examples, the state machine 300 may start at the invalid state 310. If the foot pedal signal indicates that one or more foot pedals 112 are pressed substantially simultaneously (≥1P) or within a threshold time interval (e.g., approximately 50 milliseconds, 100 milliseconds, 200 milliseconds, etc.), then the state machine 300 remains in the invalid state 310. The control signal generated based on remaining in the invalid state will cause the generators 140, 150 to not activate any of the surgical devices 162-168. Additionally, if the surgical device signal and/or the foot pedal signal indicates that any of the surgical devices 162-168 or foot pedals 112 are not connected to the system properly or are malfunctioning (e.g., a foot pedal signal is output, but a proximity sensor does not detect an object near that pedal), then the state machine 300 remains in the invalid state 310. Again, the control signal generated based on remaining in the invalid state will cause the generators 140, 150 to not activate any of the surgical devices 162-168.

The state machine 300 will transition from the invalid state 310 to the hold state 320 when the foot pedal signal indicates that zero pedals (0P) are pressed and the surgical device signal and/or the foot pedal signal indicates that the surgical devices 162-168 and the foot pedals 112 are connected to the system and functioning properly. As the state machine 300 transitions from the invalid state 310 to the hold state 320, the state machine 300 will generate the control signal to cause the generators 140, 150 to not activate any of the surgical devices 162-168. The state machine 300 will remain in the hold state 320 if the foot pedal signal indicates that zero pedals are pressed so that the control signal generated based on remaining in the hold state will again cause the generators 140, 150 to not activate any of the surgical devices 162-168. The state machine 300 will transition from the hold state 320 to the invalid state 310 if the foot pedal signal indicates that multiple foot pedals 112 are pressed substantially simultaneously (>1P). As the state machine 300 transitions from the hold state 320 to the invalid state 310, the state machine 300 will generate the control signal to cause the generators 140, 150 to not activate any of the surgical devices 162-168.

In some examples, the state machine 300 will transition from the hold state 320 to the single press active state 330 when the foot pedal signal indicates that a first foot pedal (1P) is pressed. As the state machine 300 transitions from the hold state 320 to the single press active state 330, the state machine 300 will generate the control signal to cause either the first generator 140 or the second generator 150 to activate the surgical device associated with the pressed first foot pedal. Which generator is used to activate the surgical device will depend on the energy modality, e.g., core energy or advanced energy, that is required to activate the surgical device associated with the pressed first foot pedal. For example, if the first generator 140 is a core energy generator, the second generator 150 is an advanced energy generator, and the surgical device associated with the pressed first foot pedal is an electrocautery instrument that uses advanced energy, then the second generator 150 will be used to activate the surgical device associated with the pressed first foot pedal. In other examples, the first generator 140 may be an advanced energy generator and the second generator 150 may be a core energy generator.

If the foot pedal signal indicates that the first foot pedal remains pressed and no other foot pedal is pressed (1P, original), then the state machine 300 will remain in the single press active state 330 and the control signal generated by the state machine 300 will continue to cause the generator to maintain the activation of the surgical device associated with the pressed first foot pedal.

The state machine 300 will transition from the single press active state 330 to the hold state 320 when the foot pedal signal indicates that the pressed first foot pedal is released and no other foot pedal is pressed. As the state machine 300 transitions from the single press active state 330 to the hold state 320, the state machine 300 will generate the control signal to cause the generator that is activating the surgical device associated with the pressed first foot pedal to deactivate the surgical device associated with the pressed first foot pedal. The state machine 300 will transition from the single press active state 330 to the invalid state 310 when the foot pedal signal indicates that one or more foot pedals are pressed substantially simultaneously and none of the pressed foot pedals are the first foot pedal (≥1P, without original). For example, if the surgeon's foot slips off of the active pedal and lands on multiple other pedals, the system may transition from the single press active state 330 to the invalid state 310. As the state machine 300 transitions from the single press active state 330 to the invalid state 310, the state machine 300 will generate the control signal to cause the generator that is activating the surgical device associated with the pressed first foot pedal to deactivate the surgical device associated with the pressed first foot pedal.

In some examples, the state machine 300 will transition from the single press active state 330 to the multiple press active state 340 when the foot pedal signal indicates that at least one additional foot pedal, the second foot pedal, is newly pressed while the first foot pedal remains pressed (>1P, with original). As the state machine 300 transitions from the single press active state 330 to the multiple press active state 340, the control signal generated by the state machine 300 will continue to cause the generator to maintain the activation of the surgical device associated with the pressed first foot pedal while not activating a second surgical device associated with the pressed second foot pedal. If the foot pedal signal indicates that the first foot pedal and the at least one additional foot pedal remain pressed or that the first foot pedal remains pressed while additional foot pedals are newly pressed, then the state machine 300 will remain in the multiple press active state 340 and the control signal generated by the state machine 300 will continue to cause the generator to maintain the activation of the surgical device associated with the pressed first foot pedal while not activating any other surgical device that is associated with any of the additional pressed foot pedals.

The state machine 300 will transition from the multiple press active state 340 to the single press active state 330 if the foot pedal signal indicates that only one foot pedal is pressed and that foot pedal is the first foot pedal. As the state machine 300 transitions from the multiple press active state 340 to the single press active state 330, the control signal generated by the state machine 300 will continue to cause the generator to maintain the activation of the surgical device associated with the pressed first foot pedal.

In some examples, the state machine 300 will transition from the multiple press active state 340 to the hold state 320 if the foot pedal signal indicates that all of the pressed foot pedals are released so that there are no pressed foot pedals. The control signal generated by the state machine 300 as the state machine transitions from the multiple press active state 340 to the hold state 320 will cause the generator to deactivate the surgical device associated with the pressed first foot pedal and to not activate any other surgical device. The state machine 300 will transition from the multiple press active state 340 to the invalid state if the foot pedal signal indicates that the first foot pedal is released while at least one additional foot pedal remains pressed. As the state machine 300 transitions from the multiple press active state 340 to the invalid state 310, the control signal generated by the state machine 300 will cause the generator to deactivate the surgical device associated with the pressed first foot pedal and to not activate any other surgical device.

In some examples, various devices in the system 100 may provide feedback to the user based on the state of the state machine 300. For example, if a generator is delivering energy to a surgical device, the generator may receive the feedback signal, such as an audio signal, from the second processor 120 to output an audio feedback, a visual feedback, a vibrotactile feedback, or any other suitable form of feedback. Additionally, if the generator is not delivering energy because the state machine 300 transitioned to the invalid state 310, then the first processor 114 may output an audio feedback, a visual feedback such as an error message, a vibrotactile feedback, or any other suitable form of feedback.

Utilizing software, such as implementations of state machine 300, to control the activation of multiple surgical devices 162-168 on a surgical platform 160 allows for a consistent handling of multiple foot pedal presses regardless of the type or number of foot pedals and generators being used in the system. This consistent handling of multiple foot pedal presses may reduce the amount accidental surgical device activation and may eliminate the amount of multiple surgical device activation, both of which may cause serious damage and harm to the patient, that occurs during surgery. And while the example shown in FIG. 3 employs a state machine architecture, software may employ a loop structure in conjunction with one or more condition checks and state variables, e.g., via a "switch" block in the C/C++/Java language or if/else blocks, as an alternative to an explicit state machine.

Figure 4:
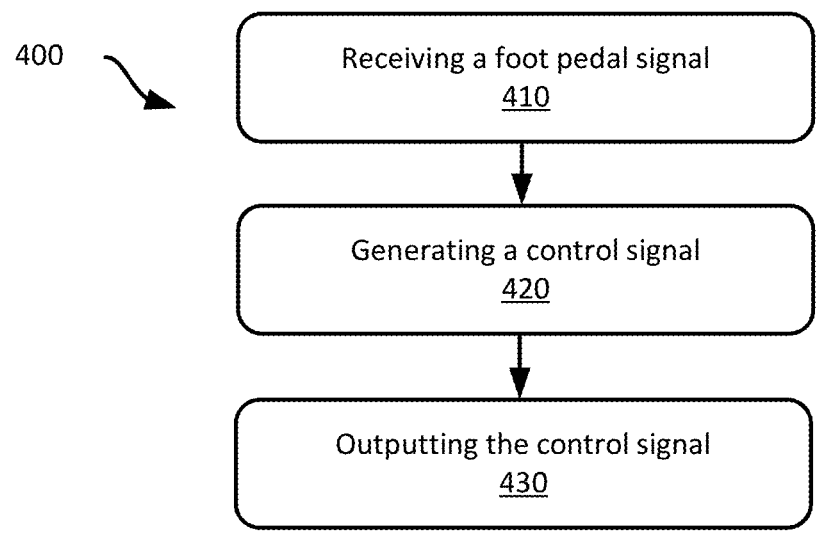
FIG. 4 shows a flowchart for an example method for controlling multiple separate generators that are used to activate multiple surgical devices connected to a single surgical platform according to this disclosure.

Referring now to FIG. 4, FIG. 4 shows an example method 400 for controlling multiple separate generators that are used to activate multiple surgical devices connected to a single surgical platform according to this disclosure. The example method 400 will be discussed with respect to the system 100 shown in FIG. 1 and the state machine 300 shown in FIG. 3. However, it should be appreciated that any suitable device for controlling multiple separate generators that are used to activate multiple surgical devices connected to a single surgical platform may be employed, such as those shown in FIG. 2 or 5.

At block 410, a foot pedal signal is received indicating an activation state (e.g., pressed or not pressed) of one or more foot pedals 112. The foot pedals 112 may be the same as those included in the foot pedal device 200 described above in reference to FIG. 2. In some examples, there may be four separate foot pedals, first foot pedal 210, second foot pedal 220, third foot pedal 230, and fourth foot pedal 240. When one or more of the foot pedals 210-240 is pressed, the foot pedal device transmits the foot pedal signal indicating which foot pedal 210-240 has been pressed and thus activated. This foot pedal signal may be received by the first processor 114 and transmitted to the second processor 120 as discussed above in reference to FIG. 1.

At block 420, a control signal is generated based on the foot pedal signal. The control signal may be generated using software, such as the state machine 300 discussed above in reference to FIG. 3. The foot pedal signal may cause the state machine to transition between states, or remain at a single state, and thus generate a control signal based on that transition.

In some examples, as discussed above in reference to FIG. 3, the state machine 300 may have four separate states substantially as discussed above. The state machine 300 may transition from the first state to the second state when the foot pedal signal indicates that a first foot pedal is pressed. The state machine 300 may transition from the second state to the third state when the foot pedal signal indicates that the first foot pedal remains pressed and a second foot pedal is newly pressed. The state machine 300 transitions from the third state to the fourth state when the foot pedal signal indicates that the first foot pedal is inactive and at least the second foot pedal remains pressed. The state machine 300 may also transition directly from the second state to the fourth state when the foot pedal signal indicates that the first foot pedal is inactive and at least the second foot pedal remains pressed. And the state machine 300 transitions from the fourth state to the first state when the foot pedal signal indicates that no foot pedal is pressed. The state machine 300 may also transition directly from the third state to the first state when the foot pedal signal indicates that no foot pedal is pressed.

The transition between states of the state machine 300 will cause the state machine to generate a control signal and transmit that control signal to the foot pedal interface board 130 discussed above. As the state machine 300 transitions between the first state and the second state, the control signal generated will cause the surgical device 162-168 associated with the pressed first foot pedal to be activated by the generator 140, 150 that provides the surgical device with the correct energy modality. As the state machine 300 transitions between the second state and the third state, the control signal generated will cause the surgical device 162-168 associated with the pressed first foot pedal to remain activated by the corresponding generator 140, 150 while no other surgical device 162-168 is activated. As the state machine 300 transitions between either the second state or the third state and the fourth state or the second state or the third state and the first state, the control signal generated will cause the surgical device 162-168 associated with the pressed first foot pedal to be deactivated by the corresponding generator 140, 150 while no other surgical device 162-168 is activated. As the state machine 300 transitions between the fourth state and the first state, none of the surgical devices 162-168 will be activated by the generators based on the control signal generated.

At block 430, the control signal generated by the software at block 420 is output either to the foot pedal interface board 130 or directly to the generators 140, 150 so as to cause the generators 140, 150 to not activate, activate, maintain the activation, or deactivate the surgical devices 162-168 based on the control signal.

Figure 5:
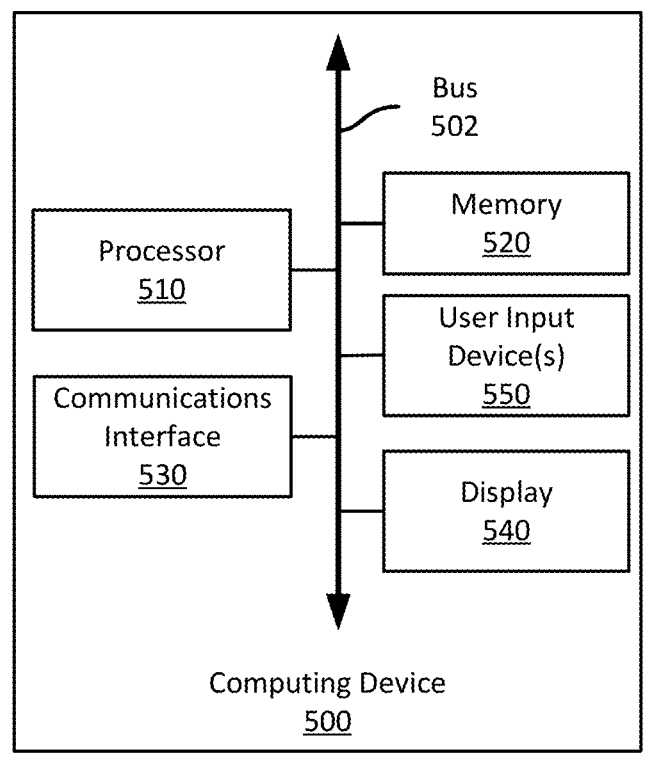
FIG. 5 shows an example computing device for controlling multiple separate generators that are used to activate multiple surgical devices connected to a single surgical platform according to this disclosure.

Referring now to FIG. 5, FIG. 5 shows an example computing device 500 suitable for use in example systems or methods for controlling multiple separate generators that are used to activate multiple surgical devices connected to a single surgical platform according to this disclosure. In this example, the example computing device 500 is an electronic device such as a mobile device, a tablet, a laptop, a computer, a wearable device such as a smart watch, etc.

The example computing device 500 includes a processor 510 which is in communication with the memory 520 and other components of the computing device 500 using one or more communications buses 502. The processor 510 executes processor-executable instructions stored in the memory 520 to assist with controlling multiple separate generators that are used to activate multiple surgical devices connected to a single surgical platform, such as instructions for part or all of the example method 400 described above with respect to FIG. 4. The computing device 500, in this example, also includes one or more user input devices 550, such as a keyboard, mouse, touchscreen, microphone, etc., to accept user input. The computing device 500 also includes a display 540 communicatively coupled to the processor 510 using the one or more communications buses 502 to provide visual output to a user. For example, the display 540 may show the current active surgical device 162-168 as described above in relation to FIG. 1.

The computing device 500 also includes a communications interface 530. In some examples, the communications interface 530 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and devices herein are described in terms of software executing on various machines, the methods and devices may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor includes a computer-readable medium, such as a random access memory (RAM) coupled to the processor. The processor executes computer-executable program instructions stored in memory, such as executing one or more computer programs. Such processors may include a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may include, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method for controlling a plurality of surgical devices, the method comprising:
   receiving a foot pedal signal to activate a first surgical device associated with a first foot pedal based on a pressing of the first foot pedal, the foot pedal signal indicating a foot pedal activation of the first foot pedal of a plurality of foot pedals;
   generating a control signal based on the foot pedal signal, wherein:
      if the foot pedal signal indicates that only the first foot pedal is pressed, then generating the control signal to cause a generator to activate the first surgical device;
      if the foot pedal signal indicates that the first foot pedal remains pressed and a second foot pedal is newly pressed to transmit a second foot pedal signal to activate a second surgical device associated with the second foot pedal, the second foot pedal signal indicating a second foot pedal activation of the second foot pedal, then generating the control signal to cause the generator to:
         maintain activation of the first surgical device associated with the first foot pedal; and
         not activate the second surgical device; and
      if the foot pedal signal indicates that the first foot pedal is released while the second foot pedal remains pressed, then generating the control signal to cause the generator to:
         deactivate the first surgical device associated with the first foot pedal, and
         not activate the second surgical device associated with the second foot pedal; and
   outputting the control signal to the generator.

2. The method of claim 1, wherein if the foot pedal signal indicates that the first foot pedal is the only foot pedal of the plurality of foot pedals pressed, then generating the control signal to cause the generator to maintain activation of the first surgical device associated with the first foot pedal.

3. The method of claim 1, wherein if the foot pedal signal indicates that the pressed first foot pedal is released, then generating the control signal to cause the generator to deactivate the first surgical device associated with the first foot pedal.

4. The method of claim 1, wherein if the foot pedal signal indicates that the second foot pedal remains pressed while the first foot pedal remains pressed, then generating the control signal to cause the generator to maintain activation of the first surgical device associated with the first foot pedal and to not activate the second surgical device associated with the second foot pedal.

5. The method of claim 1, wherein if the foot pedal signal indicates that the first foot pedal is pressed, the second foot pedal is pressed while the first foot pedal remains pressed, and the second foot pedal is released while the first foot pedal remains pressed, then generating the control signal to cause the generator to maintain activation of the first surgical device associated with the first foot pedal.

6. The method of claim 1, wherein if the foot pedal signal indicates that the pressed first foot pedal is released substantially simultaneously as the second foot pedal is pressed, then generating the control signal to cause the generator to deactivate the first surgical device associated with the first foot pedal.

7. The method of claim 1, wherein determining the control signal based on the foot pedal signal comprises utilising a state machine, the state machine comprising a plurality of states, wherein:
a first state corresponds to no foot pedals active;
a second state corresponds to a single foot pedal active;
a third state corresponds to multiple foot pedals active; and
a fourth state corresponds to an invalid combination of foot pedals active.

8. The method of claim 7, wherein the state machine transitions from the first state to the second state when the foot pedal signal indicates that the first foot pedal is pressed.

9. The method of claim 7, wherein the state machine transitions from the second state to the third state when the foot pedal signal indicates that the first foot pedal remains pressed and the second foot pedal is newly pressed.

10. The method of claim 7, wherein the state machine transitions from the third state to the fourth state when the foot pedal signal indicates that the first foot pedal is inactive and the second foot pedal remains pressed.

11. The method of claim 7, wherein the state machine transitions from the fourth state to the first state when the foot pedal signal indicates that no foot pedal is pressed.

12. The method of claim 1, further comprising transmitting an audio signal based on the generated control signal and outputting audio feedback based on the audio signal.

13. The method of claim 1, wherein at least one proximity sensor is coupled to the plurality of foot pedals, the proximity sensor communicatively coupled to a processor and configured to detect the presence of an object proximate to the plurality of foot pedals; the processor configured to:
receive a sensor signal from the proximity sensor;
generate an error feedback signal based on the sensor signal, wherein:
if the sensor signal indicates that the first foot pedal is pressed and the proximity sensor coupled to the first foot pedal does not detect the presence of the object, then generating the error feedback signal to provide feedback to a user indicating the first foot pedal is inadvertently pressed; and
output the error feedback signal to a feedback device.

14. The method of claim 13, wherein the feedback device is configured to output at least one of audio feedback, visual feedback, or tactile feedback.

15. A system comprising:
a plurality of foot pedals;
at least one generator; and
at least one processor communicatively coupled to the plurality of foot pedals and the at least one generator, the at least one processor configured to:
receive a foot pedal signal to activate a first surgical device associated with a first foot pedal based on a pressing of the first foot pedal, the foot pedal signal indicating a foot pedal activation of the first foot pedal of the plurality of foot pedals;
generate a control signal based on the foot pedal signal, wherein:
if the foot pedal signal indicates that only the first foot pedal is pressed, then generating the control signal to cause the at least one generator to activate the first surgical device;
if the foot pedal signal indicates that the first foot pedal remains pressed and a second foot pedal is newly pressed to transmit a second foot pedal signal to activate a second surgical device associated with the second foot pedal, the second foot pedal signal indicating a second foot pedal activation of the second foot pedal, then generating the control signal to cause the at least one generator to:
maintain activation of the first surgical device associated with the first foot pedal; and
not activate the second surgical device; and
if the foot pedal signal indicates that the first foot pedal is released while the second foot pedal remains pressed, then generating the control signal to cause the at least one generator to:
deactivate the first surgical device associated with the first foot pedal; and
not activate the second surgical device associated with the second foot pedal; and
outputting the control signal to the at least one generator.

16. The system of claim 15, wherein if the foot pedal signal indicates that the first foot pedal is the only foot pedal of the plurality of foot pedals pressed, then generating the control signal to cause the generator to maintain activation of the first surgical device associated with the first foot pedal.

17. The system of claim 15, wherein if the foot pedal signal indicates that the pressed first foot pedal is released, then generating the control signal to cause the generator to deactivate the first surgical device associated with the first foot pedal.

18. The system of claim 15, wherein if the foot pedal signal indicates that the second foot pedal remains pressed while the first foot pedal remains pressed, then generating the control signal to cause the generator to maintain activation of the first surgical device associated with the first foot pedal and to not activate the second surgical device associated with the second foot pedal.

19. The system of claim 15, wherein if the foot pedal signal indicates that the first foot pedal is pressed, the second foot pedal is pressed while the first foot pedal remains pressed, and the second foot pedal is released while the first foot pedal remains pressed, then generating the control signal to cause the generator to maintain activation of the first surgical device associated with the first foot pedal.

20. The system of claim 15, wherein if the foot pedal signal indicates that the pressed first foot pedal is released substantially simultaneously as the second foot pedal is pressed, then generating the control signal to cause the generator to deactivate the first surgical device associated with the first foot pedal.

21. The system of claim 15, wherein determining the control signal based on the foot pedal signal comprises utilising a state machine, the state machine comprising a plurality of states, wherein:
a first state corresponds to no foot pedals active;
a second state corresponds to a single foot pedal active;
a third state corresponds to multiple foot pedals active; and
a fourth state corresponds to an invalid combination of foot pedals active.

22. The system of claim 21, wherein the state machine transitions from the first state to the second state when the foot pedal signal indicates that the first foot pedal is pressed.

23. The system of claim 21, wherein the state machine transitions from the second state to the third state when the foot pedal signal indicates that the first foot pedal remains pressed and the second foot pedal is newly pressed.

24. The system of claim 21, wherein the state machine transitions from the third state to the fourth state when the foot pedal signal indicates that the first foot pedal is inactive and the second foot pedal remains pressed.

25. The system of claim 21, wherein the state machine transitions from the fourth state to the first state when the foot pedal signal indicates that no foot pedal is pressed.

26. The system of claim 15, further comprising transmitting an audio signal based on the generated control signal and outputting audio feedback based on the audio signal.

27. The system of claim 15, wherein at least one proximity sensor is coupled to the plurality of foot pedals, the proximity sensor communicatively coupled to the at least one processor and configured to detect the presence of an object proximate to the plurality of foot pedals; the at least one processor further configured to:
  receive a sensor signal from the proximity sensor;
  generate an error feedback signal based on the sensor signal, wherein:
    if the sensor signal indicates that the first foot pedal is pressed and the proximity sensor coupled to the first foot pedal does not detect the presence of the object, then generating the error feedback signal to provide feedback to a user indicating the first foot pedal is inadvertently pressed; and
  output the error feedback signal to a feedback device.

28. The system of claim 27, wherein the feedback device is configured to output at least one of audio feedback, visual feedback, or tactile feedback.

29. A non-transitory computer readable medium comprising program code, which when executed by a processor is configured to cause the processor to:
  receive a foot pedal signal to activate a first surgical device associated with a first foot pedal based on a pressing of the first foot pedal, the foot pedal signal indicating a foot pedal activation of the first foot pedal of a plurality of foot pedals;
  generate a control signal based on the foot pedal signal, wherein:
    if the foot pedal signal indicates that only the first foot pedal is pressed, then generating the control signal to cause a generator to activate the first surgical device;
    if the foot pedal signal indicates that the first foot pedal remains pressed and a second foot pedal is newly pressed to transmit a second foot pedal signal to activate a second surgical device associated with the second foot pedal, the second foot pedal signal indicating a second foot pedal activation of the second foot pedal, then generating the control signal to cause the generator to:
      maintain activation of the first surgical device associated with the first foot pedal; and
      not activate the second surgical device; and
    if the foot pedal signal indicates that the first foot pedal is released while the second foot pedal remains, then generating the control signal to cause the generator to:
      deactivate the first surgical device associated with the first foot pedal, and
      not activate the second surgical device associated with the second foot pedal; and
  output the control signal to a generator.

30. The non-transitory computer readable medium of claim 29, wherein if the foot pedal signal indicates that the first foot pedal is the only foot pedal of the plurality of foot pedals pressed, then generating the control signal to cause the generator to maintain activation of the first surgical device associated with the first foot pedal.

31. The non-transitory computer readable medium of claim 29, wherein if the foot pedal signal indicates that the pressed first foot pedal is released, then generating the control signal to cause the generator to deactivate the first surgical device associated with the first foot pedal.

32. The non-transitory computer readable medium of claim 29, wherein if the foot pedal signal indicates that the second foot pedal remains pressed while the first foot pedal remains pressed, then generating the control signal to cause the generator to maintain activation of the first surgical device associated with the first foot pedal and to not activate the second surgical device associated with the second foot pedal.

33. The non-transitory computer readable medium of claim 29, wherein if the foot pedal signal indicates that the first foot pedal is pressed, the second foot pedal is pressed while the first foot pedal remains pressed, and the second foot pedal is released while the first foot pedal remains pressed, then generating the control signal to cause the generator to maintain activation of the first surgical device associated with the first foot pedal.

34. The non-transitory computer readable medium of claim 29, wherein if the foot pedal signal indicates that the pressed first foot pedal is released substantially simultaneously as the second foot pedal is pressed, then generating the control signal to cause the generator to deactivate the first surgical device associated with the first foot pedal.

35. The non-transitory computer readable medium of claim 29, wherein determining the control signal based on the foot pedal signal comprises utilising a state machine, the state machine comprising a plurality of states, wherein:
  a first state corresponds to no foot pedals active;
  a second state corresponds to a single foot pedal active;
  a third state corresponds to multiple foot pedals active; and
  a fourth state corresponds to an invalid combination of foot pedals active.

36. The non-transitory computer readable medium of claim 35, wherein the state machine transitions from the first state to the second state when the foot pedal signal indicates that the first foot pedal is pressed.

37. The non-transitory computer readable medium of claim 35, wherein the state machine transitions from the second state to the third state when the foot pedal signal indicates that the first foot pedal remains pressed and the second foot pedal is newly pressed.

38. The non-transitory computer readable medium of claim 35, wherein the state machine transitions from the third state to the fourth state when the foot pedal signal indicates that the first foot pedal is inactive and the second foot pedal remains pressed.

39. The non-transitory computer readable medium of claim 35, wherein the state machine transitions from the fourth state to the first state when the foot pedal signal indicates that no foot pedal is pressed.

40. The non-transitory computer readable medium of claim 29, further comprising transmitting an audio signal based on the generated control signal and outputting audio feedback based on the audio signal.

41. The non-transitory computer readable medium of claim 29, wherein at least one proximity sensor is coupled to the plurality of foot pedals, the proximity sensor communicatively coupled to the processor and configured to detect the presence of an object proximate to the plurality of foot pedals; the non-transitory computer readable medium comprising program code further configured to cause the processor to:
  receive a sensor signal from the proximity sensor;
  generate an error feedback signal based on the sensor signal, wherein:

if the sensor signal indicates that the first foot pedal is pressed and the proximity sensor coupled to the first foot pedal does not detect the presence of the object, then generating the error feedback signal to provide feedback to a user indicating the first foot pedal is inadvertently pressed; and output the error feedback signal to a feedback device.

42. The non-transitory computer readable medium of claim 41, wherein the feedback device is configured to output at least one of audio feedback, visual feedback, or tactile feedback.

\* \* \* \* \*